(12) United States Patent
Doxey et al.

(10) Patent No.: US 9,855,211 B2
(45) Date of Patent: Jan. 2, 2018

(54) TOPICAL COMPOSITIONS AND METHODS OF USING THE SAME

(71) Applicant: Novan, Inc., Durham, NC (US)

(72) Inventors: Ryan Doxey, Raleigh, NC (US); Adam Sabouni, Cary, NC (US); Eleftherios Kougoulos, Morrisville, NC (US); Nathan Stasko, Durham, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

(21) Appl. No.: 14/191,958

(22) Filed: Feb. 27, 2014

(65) Prior Publication Data

US 2014/0242023 A1 Aug. 28, 2014

Related U.S. Application Data

(60) Provisional application No. 61/770,615, filed on Feb. 28, 2013.

(51) Int. Cl.
*A61K 47/48* (2006.01)
*A61K 9/00* (2006.01)
*A61K 47/10* (2017.01)
*A61K 47/12* (2006.01)
*A61K 9/06* (2006.01)
*A61K 47/32* (2006.01)
*A61K 33/00* (2006.01)
*A61K 47/69* (2017.01)

(52) U.S. Cl.
CPC ............ *A61K 9/0014* (2013.01); *A61K 9/06* (2013.01); *A61K 33/00* (2013.01); *A61K 47/10* (2013.01); *A61K 47/12* (2013.01); *A61K 47/32* (2013.01); *A61K 47/6923* (2017.08)

(58) Field of Classification Search
CPC ............ A61K 9/0014; A61K 47/48861; A61K 47/10; A61K 33/00; A61K 9/06; A61K 47/32; A61K 47/12
See application file for complete search history.

(56) References Cited

U.S. PATENT DOCUMENTS

| 3,754,368 A | 8/1973 | Moore et al. |
| 4,182,827 A | 1/1980 | Jones et al. |
| 4,829,092 A | 5/1989 | Nelson et al. |
| 4,917,886 A | 4/1990 | Asche et al. |
| 5,405,919 A | 4/1995 | Keefer |
| 5,519,020 A | 5/1996 | Smith et al. |
| 5,691,423 A | 11/1997 | Smith et al. |
| 5,770,645 A | 6/1998 | Stamler et al. |
| 5,814,656 A | 9/1998 | Saavedra et al. |
| 5,814,666 A | 9/1998 | Green et al. |
| 5,840,759 A | 11/1998 | Mitchell et al. |
| 5,910,316 A | 6/1999 | Keefer et al. |
| 5,912,008 A | 6/1999 | Horstmann et al. |
| 5,958,427 A | 9/1999 | Salzman et al. |
| 5,968,528 A | 10/1999 | Deckner et al. |
| 6,103,266 A | 8/2000 | Tapolsky et al. |
| 6,103,275 A * | 8/2000 | Seitz .................... A61K 9/0014 424/718 |
| 6,110,453 A | 8/2000 | Keefer et al. |
| 6,303,141 B1 | 10/2001 | Fischer et al. |
| 6,382,526 B1 | 5/2002 | Reneker et al. |
| 6,465,445 B1 | 10/2002 | Labrie |
| 6,520,425 B1 | 2/2003 | Reneker |
| 6,695,992 B2 | 2/2004 | Reneker |
| 6,719,997 B2 | 4/2004 | Hsu et al. |
| 6,737,447 B1 | 5/2004 | Smith et al. |
| 6,818,018 B1 | 11/2004 | Sawhney |
| 6,861,064 B1 | 3/2005 | Laakso et al. |
| 7,048,951 B1 | 5/2006 | Seitz et al. |
| 7,704,518 B2 | 4/2010 | Tamarkin et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,486,451 B2 | 7/2013 | Morris et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,722,103 B2 | 5/2014 | Morris et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,265,725 B2 | 2/2016 | Tamarkin et al. |
| 9,320,705 B2 | 4/2016 | Tamarkin et al. |
| 2002/0012816 A1 | 1/2002 | Shimizu et al. |

(Continued)

FOREIGN PATENT DOCUMENTS

| BR | WO 2009067095 A1 * | 5/2009 | ............... A61K 8/97 |
| CA | 2 594 407 A1 | 8/2006 | |

(Continued)

OTHER PUBLICATIONS

Amadeu et al. "Nitric Oxide Donor Improves Healing if Applied on Inflammatory and Proliferative Phase" *Journal of Surgical Research* 149:84-93 (2008).
Bohl-Masters et al. "Effects of nitric oxide releasing poly(vinyl alcohol) hydrogel dressings on dermal wound healing in diabetic mice" *Wound Repair and Regeneration* 10(5):286-294 (2002).
Hetrick et al. "Anti-biofilm efficacy of nitric oxide-releasing silica nanoparticles" *Biomaterials* 30:2782-2789 (2009).
International Search Report and the Written Opinion of the International Searching Authority corresponding to International Patent Application No. PCT/US2014/019536; dated Jul. 28, 2014.

(Continued)

*Primary Examiner* — Anoop Singh
*Assistant Examiner* — Doan Phan
(74) *Attorney, Agent, or Firm* — Myers Bigel, P.A.

(57) ABSTRACT

The present invention relates generally to topical compositions and methods of using the same.

24 Claims, 8 Drawing Sheets

(56) References Cited

U.S. PATENT DOCUMENTS

| | | |
|---|---|---|
| 2002/0013304 A1 | 1/2002 | Wilson et al. |
| 2002/0028223 A1 | 3/2002 | Vatter et al. |
| 2002/0082221 A1 | 6/2002 | Herrmann et al. |
| 2002/0094985 A1 | 7/2002 | Herrmann et al. |
| 2002/0122771 A1 | 9/2002 | Holland et al. |
| 2002/0136750 A1 | 9/2002 | Benjamin et al. |
| 2002/0155174 A1 | 10/2002 | Benjamin et al. |
| 2003/0077243 A1 | 4/2003 | Fitzhugh |
| 2003/0159702 A1 | 8/2003 | Lindell et al. |
| 2003/0175328 A1 | 9/2003 | Shefer et al. |
| 2003/0205234 A1 | 11/2003 | Bardach et al. |
| 2003/0235605 A1 | 12/2003 | Lelah et al. |
| 2004/0009238 A1 | 1/2004 | Miller et al. |
| 2004/0043068 A1 | 3/2004 | Tedeschi et al. |
| 2004/0068005 A1 | 4/2004 | Szilvassy et al. |
| 2004/0171589 A1 | 9/2004 | Herrmann et al. |
| 2004/0202684 A1* | 10/2004 | Djerassi ............... A61K 8/02 424/401 |
| 2004/0220260 A1 | 11/2004 | Cals-Grierson |
| 2004/0265244 A1 | 12/2004 | Rosen |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0160897 A1 | 7/2006 | Pelicci et al. |
| 2006/0173076 A1 | 8/2006 | Vishnupad et al. |
| 2006/0269620 A1 | 11/2006 | Morris et al. |
| 2006/0275218 A1 | 12/2006 | Tamarkin et al. |
| 2007/0166255 A1 | 7/2007 | Gupta |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0071206 A1 | 3/2008 | Peters |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311163 A1* | 12/2008 | Peters ............... A61K 8/0208 424/401 |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0068248 A1 | 3/2009 | Waterhouse et al. |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2009/0226380 A1 | 9/2009 | Clark et al. |
| 2009/0297634 A1 | 12/2009 | Friedman et al. |
| 2010/0098733 A1 | 4/2010 | Stasko |
| 2010/0221195 A1 | 9/2010 | Tamarkin et al. |
| 2010/0266510 A1 | 10/2010 | Tamarkin et al. |
| 2010/0286285 A1 | 11/2010 | Barthez et al. |
| 2010/0310476 A1 | 12/2010 | Tamarkin et al. |
| 2010/0331968 A1 | 12/2010 | Morris et al. |
| 2011/0027369 A1 | 2/2011 | Franke |
| 2011/0045037 A1 | 2/2011 | Tamarkin et al. |
| 2011/0052650 A1 | 3/2011 | Morris et al. |
| 2011/0082167 A1 | 4/2011 | Pisak et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2012/0114547 A1 | 5/2012 | Smith |
| 2012/0134951 A1 | 5/2012 | Stasko et al. |
| 2012/0136323 A1 | 5/2012 | Stasko et al. |
| 2012/0141384 A1 | 6/2012 | Tamarkin et al. |
| 2012/0156163 A1 | 6/2012 | Bauman et al. |
| 2012/0237453 A1 | 9/2012 | Tamarkin et al. |
| 2013/0059017 A1 | 3/2013 | Perricone et al. |
| 2013/0109756 A1 | 5/2013 | Huber et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2013/0310533 A1 | 11/2013 | Bao et al. |
| 2013/0344334 A1 | 12/2013 | Schoenfisch et al. |
| 2014/0017121 A1 | 1/2014 | Schoenfisch et al. |
| 2014/0057001 A1 | 2/2014 | Bauman et al. |
| 2014/0058124 A1 | 2/2014 | Schoenfisch et al. |
| 2014/0065200 A1 | 3/2014 | Schoenfisch et al. |
| 2014/0107071 A1 | 4/2014 | Kougoulos et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0242023 A1 | 8/2014 | Doxey et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2014/0369949 A1 | 12/2014 | Peters |
| 2015/0017103 A1 | 1/2015 | Tamarkin et al. |
| 2015/0024052 A1 | 1/2015 | Doxey |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0141606 A1 | 5/2015 | Bao et al. |
| 2015/0182543 A1 | 7/2015 | Schoenfisch et al. |
| 2015/0225488 A1 | 8/2015 | Schoenfisch et al. |

FOREIGN PATENT DOCUMENTS

| | | | |
|---|---|---|---|
| EP | 1 300 424 A1 | 4/2003 | |
| EP | 1 707 224 A1 | 10/2006 | |
| EP | 1 861 130 B1 | 9/2008 | |
| EP | 1 871 433 B1 | 4/2009 | |
| EP | 1 846 058 B1 | 7/2009 | |
| EP | 2 119 459 A1 | 11/2009 | |
| EP | 2 142 179 A1 | 1/2010 | |
| EP | 2 142 181 A1 | 1/2010 | |
| EP | 1 917 005 B1 | 9/2010 | |
| GB | WO 93/10754 | * 6/1993 | ............... A61K 7/48 |
| GB | 2 354 441 | 3/2001 | |
| WO | WO 96/13164 A1 | 5/1996 | |
| WO | WO 96/15797 A1 | 5/1996 | |
| WO | WO 98/05689 A1 | 2/1998 | |
| WO | WO 00/02593 A2 | 1/2000 | |
| WO | WO 00/49993 A2 | 8/2000 | |
| WO | WO 01/26702 A2 | 4/2001 | |
| WO | WO 01/85013 A2 | 11/2001 | |
| WO | WO 02/20026 A2 | 3/2002 | |
| WO | WO 02/41902 A1 | 5/2002 | |
| WO | WO 02/056864 A2 | 7/2002 | |
| WO | WO 03/013489 A1 | 2/2003 | |
| WO | WO 03/072039 A2 | 9/2003 | |
| WO | WO 03/078437 A1 | 9/2003 | |
| WO | WO 03/086282 A2 | 10/2003 | |
| WO | WO 03/092763 A1 | 11/2003 | |
| WO | WO 2004/012659 A2 | 2/2004 | |
| WO | WO 2004/012874 A1 | 2/2004 | |
| WO | WO 2004/098538 A2 | 11/2004 | |
| WO | WO 2005/003032 A1 | 1/2005 | |
| WO | WO 2005/004984 A1 | 1/2005 | |
| WO | WO 2005/011575 A2 | 2/2005 | |
| WO | WO 2005/037339 A1 | 4/2005 | |
| WO | WO 2005/046661 A2 | 5/2005 | |
| WO | WO 2006/084910 A2 | 8/2006 | |
| WO | WO 2006/084912 A1 | 8/2006 | |
| WO | WO 2006/100154 A1 | 9/2006 | |
| WO | WO 2006/128121 A2 | 11/2006 | |
| WO | WO 2006/138035 A1 | 12/2006 | |
| WO | WO 2007/007208 A2 | 1/2007 | |
| WO | WO 2007/023005 A1 | 3/2007 | |
| WO | WO 2007/023396 A2 | 3/2007 | |
| WO | WO 2007/054818 A2 | 5/2007 | |
| WO | WO 2007/085254 A1 | 8/2007 | |
| WO | WO 2008/032212 A2 | 3/2008 | |
| WO | WO 2008/038140 A2 | 4/2008 | |
| WO | WO 2008/038147 A2 | 4/2008 | |

(56) References Cited

FOREIGN PATENT DOCUMENTS

| | | |
|---|---|---|
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2011/005846 A1 | 1/2011 |
| WO | WO 2011/022652 A1 | 2/2011 |
| WO | WO 2011/022680 A2 | 2/2011 |
| WO | WO 2011022652 A1 * 2/2011 ........... A61K 9/0014 |
| WO | WO 2011/061519 A2 | 5/2011 |
| WO | WO 2012/100174 A1 | 7/2012 |
| WO | WO 2012/153331 A2 | 11/2012 |
| WO | WO 2013/006608 A1 | 1/2013 |
| WO | WO 2013/006613 A1 | 1/2013 |
| WO | WO 2013/138073 A1 | 9/2013 |
| WO | WO 2013/138075 A1 | 9/2013 |
| WO | WO 2015/021382 A2 | 2/2015 |

OTHER PUBLICATIONS

U.S. Appl. No. 14/133,973, filed Dec. 19, 2013, Kougoulos et al.
U.S. Appl. No. 14/771,138, filed Aug. 27, 2015, Doxey et al.
International Preliminary Report on Patentability corresponding to International Patent Application No. PCT/US2014/019536 (13 pages) (dated Sep. 11, 2015).
Al-Sa'Doni et al. "S-Nitrosothiols: a class of nitric oxide-donor drugs" *Clinical Science* 98:507-520 (2000).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
Pulfer et al. "Incorporation of nitric oxide-releasing crosslinked polyethyleneimine microspheres into vascular grafts" *Journal of Biomedical Materials Research* 37:182-189 (1997).
Sangster, James "Octanol-Water Partition Coefficients of Simple Organic Compounds" *Journal of Physical and Chemical Reference Data* 18(3):1111-1227 (1989).
Smith et al. "Transdermal delivery of nitric oxide from diazeniumdiolates" *Journal of Controlled Release* 51:153-159 (1998).
Wang et al. "Nitric Oxide Donors: Chemical Activities and Biological Applications" *Chemical Reviews* 102:1091-1134 (2002).
Boykin et al. "HBO Mediates Increased Nitric Oxide Production Associated With Wound Healing" *Wound Repaid and Regeneration* 12(2):A15 (Abstract 054) (2004).
Extended European Search Report corresponding to European Patent Application No. 14756266.4 (6 pages) (dated Aug. 2, 2016).
Peyrot et al. English Machine Translation of International Patent Application Publication No. WO 2000/002593 *Espacenet* (6 pages) (Retrieved on Sep. 27, 2016).
Office Action issued for related Chinese Patent Application No. 201480023840.8 (31 pages) (dated Jul. 31, 2017).
Kandavilli et al. "Polymers in Transdermal Drug Delivery Systems" *Pharmaceutical Technology* pp. 62-80 (2002).
Office Action issued for related Japanese Patent Application No.: 2015-560366 (9 pages) (dated Sep. 15, 2017).

\* cited by examiner

TOPICAL COMPOSITIONS AND METHODS OF USING THE SAME

RELATED APPLICATION DATA

This application claims the benefit, under 35 U.S.C. §119, of U.S. Provisional Application Ser. No. 61/770,615, filed Feb. 28, 2013, the entire contents of which is hereby incorporated by reference herein.

FIELD OF THE INVENTION

The present invention relates generally to topical compositions and methods of using the same.

BACKGROUND OF THE INVENTION

Skin disorders as well as wounds may be topically treated with various pharmaceutical compositions. Compositions that may provide different features than those provided in a pharmaceutical composition may be desired.

The present invention addresses previous shortcomings in the art by providing topical compositions and methods of using the topical compositions.

SUMMARY OF THE INVENTION

A first aspect of the present invention comprises a composition comprising a first viscosity increasing agent; at least one polyhydric alcohol; at least one buffering agent; at least one preservative; a second viscosity increasing agent; at least one organic solvent; at least one humectant; at least one active pharmaceutical ingredient; and water, wherein the composition is buffered to a pH of about 3 to about 8.

A second aspect of the present invention comprises a composition comprising at least one polyhydric alcohol present in an amount of about 1% to about 30% by weight of the composition; at least one viscosity increasing agent present in an amount of about 0.1% to about 5% by weight of the composition; water present in an amount of about 70% to about 99% by weight of the composition; at least one buffering agent present in an amount of about 0.01% to about 2% by weight of the composition; and at least one preservative present in an amount of about 0.01% to about 1% by weight of the composition; wherein the composition is buffered to a pH of about 3 to about 8.

A further aspect of the present invention comprises a kit comprising a first composition comprising at least one polyhydric alcohol present in an amount of about 1% to about 30% by weight of the composition; at least one viscosity increasing agent present in an amount of about 0.1% to about 5% by weight of the composition; and water present in an amount of about 70% to about 99% by weight of the composition; and a second composition, wherein the second composition is anhydrous.

Another aspect of the present invention comprises a method of increasing the release of nitric oxide from an anhydrous topical gel containing a diazeniumdiolate modified macromolecule comprising: contacting the anhydrous topical gel with a hydrogel having a pH of 4 to 6 to provide a combined composition; and applying the combined composition to the skin of a subject.

A further aspect of the present invention comprises a pharmaceutical composition comprising: an anhydrous topical gel comprising a diazeniumdiolate modified polysiloxane molecule; and a hydrogel comprising means for reducing the pH of the anhydrous topical gel.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION OF THE INVENTION

Figure 1:
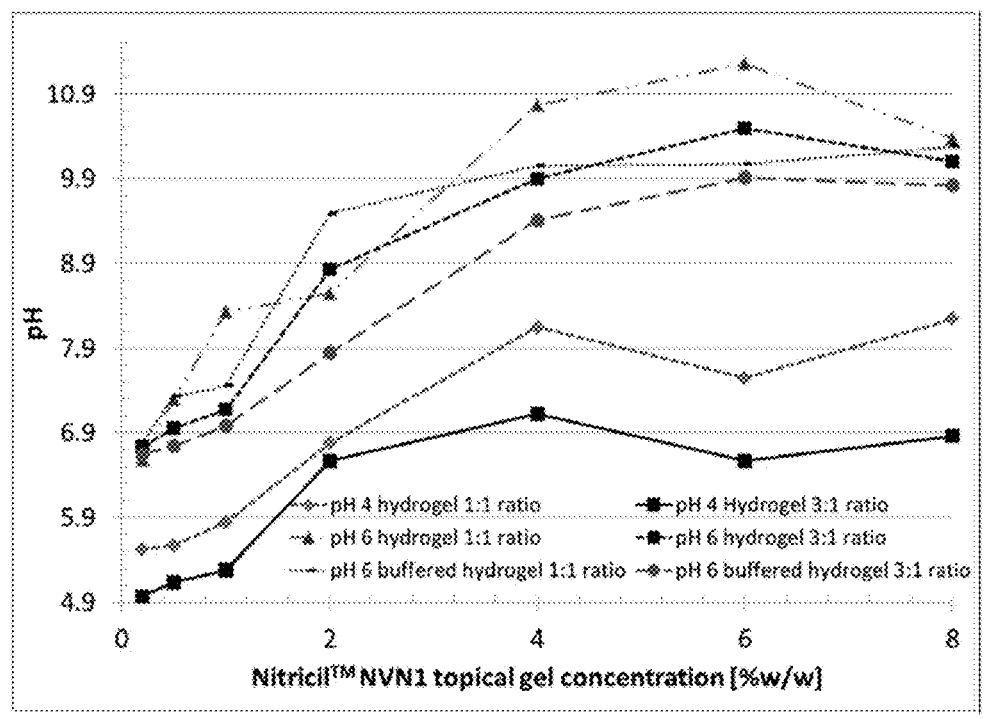
FIG. 1 shows a graph of the effects of Nitricil™ NVN1 Topical Gel strength, hydrogel pH, and hydrogel to Nitricil™ NVN1 Topical Gel ratio on the admixture pH.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

The term "about," as used herein when referring to a measurable value such as an amount or concentration and the like, is meant to encompass variations of ±10%, +5%, ±1%, ±0.5%, or even ±0.1% of the specified value as well as the specified value. For example, "about X" where X is the measurable value, is meant to include X as well as variations of ±10%, ±5%, +1%, ±0.5%, or even 0.1% of X. A range provided herein for a measureable value may include any other range and/or individual value therein.

According to some embodiments of the present invention, provided herein are topical compositions. In some embodiments a topical composition of the present invention is in the form of a hydrogel. "Hydrogel," as used herein, refers to a hydrophilic gel comprising a gel matrix and water. In some embodiments, a topical composition of the present invention comprises at least one polyhydric alcohol, at least one viscosity increasing agent, and water.

Exemplary polyhydric alcohols that may be present in a composition of the present invention include, but are not limited to, glycerol, propylene glycol, polyethylene glycol, polypropylene glycol, triethylene glycol, neopental glycols, triethanolamine, diethanolamine, ethanolamione, butylene glycol, polyethylene glycol, n-methyl diethanolamine, isopropanolamine, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a composition of the present invention comprises glycerol, such as, but not limited to, anhydrous glycerol.

A polyhydric alcohol may be present in a composition of the present invention in an amount of about 1% to about 30% by weight of the composition or any range and/or individual value therein, such as, but not limited to, about 1% to about 20% or about 5% to about 15% by weight of the composition. In certain embodiments, a polyhydric alcohol is present in a composition of the present invention in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the composition or any range and/or individual value therein.

Exemplary viscosity increasing agents that may be present in a composition of the present invention include, but are not limited to, a carboxypolymethylene; a polyacrylic polymer such as polyacrylic acid, a polyacrylate polymer, a cross-linked polyacrylate polymer, a cross-linked polyacrylic acid, and mixtures thereof; a cellulose ether such as hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof; a methacrylate; a polyvinylpyrollidone; cross-linked polyvinyl pyrrolidone; polyvinylpyrrolidone-vinyl acetate copolymer; polyvinylalcohol; polyethylene oxide; polyethylene glycol; polyvinylalkyl ether-maleic acid copolymer; a carboxy vinyl polymer; a polysaccharide; a gum such as sodium alginate, carrageenan, xantham gum, gum acacia, arabic gum, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof.

In some embodiments, a composition of the present invention comprises a carboxypolymethylene, such as, but not limited to, those commercially available from Lubrizol Corporation of Wickliffe, Ohio under the trade name Carbopol®. Exemplary Carbopol® polymers that may be present in a composition of the present invention include, but are not limited to, Carbopol® 974P NF polymer, such as Type A, Type B and/or Type C Homopolymers; Carbopol® Ultrez 10, 20, 21 NF polymer; Carbopol® 971P NF polymer; Carpobol® 980P polymer, Carbopol® ETD 2020 NF polymer, [Carbopol® 71 G NF polymer, Carbopol® 981P NF polymer, Carbopol® 970P NF polymer, Carbopol® 981 P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NF polymer, Carbopol® TR1 NF polymer, Carbopol® TR2 NF polymer, Lubrizol Aqua CC polymer and SF-2 polymer, and any combination thereof.

A viscosity increasing agent may be present in a composition of the present invention. In some embodiments, a composition of the present invention comprises at least two viscosity increasing agents that may be the same or different. In some embodiments, a first viscosity increasing agent may be present in a composition of the present invention in an amount of about 0.01% to about 5% by weight of the composition or any range and/or individual value therein, such as, but not limited to, about 0.05% to about 3% or about 0.1% to about 1.5% by weight of the composition. In certain embodiments, a first viscosity increasing agent is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition or any range and/or individual value therein.

Water may be present in a composition of the present invention in an amount of about 70% to about 99% by weight of the composition or any range and/or individual value therein, such as, but not limited to, about 75% to about 95% or about 80% to about 90% by weight of the composition. In certain embodiments, water is present in a composition of the present invention in an amount of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the composition or any range and/or individual value therein.

In some embodiments, a composition of the present invention comprises at least one polyhydric alcohol present in an amount of about 1% to about 30% by weight of the composition, at least one viscosity increasing agent present in an amount of about 0.1% to about 5% by weight of the composition, and water present in an amount of about 70% to about 99% by weight of the composition. The composition may be in the form of a hydrogel. In certain embodiments, the viscosity increasing agent may be a carboxypolymethylene.

A composition of the present invention may comprise a preservative. A preservative may be present in a composition of the present invention in an amount of about 0.01% to about 1% by weight of the composition or any range and/or individual value therein, such as, but not limited to, about 0.05% to about 1% or about 0.1% to about 1% by weight of the composition. In certain embodiments, a preservative is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the composition or any range and/or individual value therein. Exemplary preservatives that may be present in a composition of the present invention include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A composition of the present invention may comprise a neutralizing agent. A neutralizing agent may be present in a composition of the present invention in an amount sufficient to provide the composition with a pH of about 3 to about 8, or any range and/or individual value therein, such as, but not limited to, about 4 to about 7 or about 6 to about 7. In some embodiments, a neutralizing agent adjusts the pH of the composition. In certain embodiments of the present invention, a neutralizing agent is present in a composition of the present invention in an amount sufficient for the composition to have a pH of about 3, 3.5, 4, 4.5, 5, 5.5, 6, 6.5, 7, 7.5, or 8 or any range and/or individual value therein. Exemplary neutralizing agents that may be present in a composition of the present invention include, but are not limited to, bases such as sodium hydroxide, potassium hydroxide, and mixtures thereof; acids such as hydrochloric acid, citric acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

A composition of the present invention may be unbuffered or buffered. In some embodiments, a composition of the present invention may be unbuffered. In other embodiments, a composition of the present invention may be buffered. Exemplary buffers that may be present in composition of the present invention include, but are not limited to, acetic acid/acetate buffers; hydrochloric acid/citrate buffers; citrophosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, NaCl, Tween buffered saline (TNT), phosphate buffered saline, Triton X-100 (PBT) and mixtures thereof; cacodylate buffers; barbital buffers; tris buffers; and any combination thereof.

In certain embodiments, a composition of the present invention may comprise a buffering agent. Exemplary buffering agents include, but are not limited to, citric acid, acetic acid, lactic acid, boric acid, succinic acid, malic acid, and any combination thereof. A buffering agent may be present in a composition of the present invention in an amount of about 0.01% to about 2% by weight of the composition or any range and/or individual value therein, such as, but not limited to, about 0.05% to about 1%, about 0.1% to about 0.5%, or about 0.1% to about 2% by weight of the composition. In certain embodiments, a buffering agent is present in a composition of the present invention in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the composition or any range and/or individual value therein.

In some embodiments, a buffer is present in a composition of the present invention in an amount sufficient for the composition to have a pH of about 3 to about 8, or any range and/or individual value therein, such as, but not limited to, about 4 to about 7 or about 6 to about 7. In certain embodiments of the present invention, a buffer is present in a composition of the present invention in an amount sufficient for the composition to have a pH of about 3, 3.5, 4, 4.5, 5, 5.5, 6, 6.5, 7, 7.5, or 8 or any range and/or individual value therein.

A composition of the present invention may be antimicrobial. In some embodiments, a composition of the present invention comprises a preservative that is present in an amount sufficient to provide antimicrobial activity to the composition. In certain embodiments, a composition of the present invention comprises at least one polyhydric alcohol present in an amount of about 1% to about 30% by weight of the composition, at least one viscosity increasing agent present in an amount of about 0.1% to about 5% by weight of the composition, water present in an amount of about 70% to about 99% by weight of the composition, and at least one preservative in an amount of about 0.01% to about 1% by weight of the composition. The composition may be buffered to have a pH in a range of about 3 to about 8 or about 6 to about 8.

A composition of the present invention may have a viscosity in a range of about 5,000 cP to about 25,000 cP or any range and/or individual value therein, such as, but not limited to, about 5,000 cP to about 20,000 cP or about 7,000 cP to about 15,000 cP. In certain embodiments, a composition of the present invention may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP or any range and/or individual value therein.

A composition of the present invention may comprise an active pharmaceutical ingredient (API). Any suitable API or combinations of APIs may be included in a composition of the present invention. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Exemplary APIs include, but are not limited to, those described in International Application Publication No. WO 2013/006608, which is incorporated herein by reference in its entirety. Alternatively, a composition of the present invention may not comprise an API. In some embodiments, a composition of the present invention does not contain a nitric oxide (NO) releasing API. The composition may comprise at least one API, but the composition does not comprise an NO releasing API.

A composition of the present may be suitable for use and/or combination with one or more, such as, but not limited to, 2, 3, 4, or more, pharmaceutical compositions that may be the same and/or different. A composition of the present invention may be used as a drug delivery system and/or a drug release system. For example, a composition of the present invention may be configured to modulate the release of an API in a second composition upon contact of the composition of the present invention (i.e., first composition) and second composition. Alternatively or in addition, a composition of the present invention may be configured to modulate the pH of a second composition upon contact of the composition of the present invention (i.e., first composition) and second composition. In some embodiments, a composition of the present invention may be configured to modulate the pH of a second composition comprising an nitric oxide (NO) releasing API and/or the release of an NO releasing API in a second composition.

"Modulate," "modulating," "modulation," and grammatical variations thereof as used herein refer to an increase or reduction in the pH of a second composition and/or the release of an API in a second composition compared to the pH of the second composition and/or the release of the API in the second composition in the absence of a composition of the present invention. As used herein, the terms "increase," "increases," "increased," "increasing" and similar terms indicate an elevation in the pH and/or release of at least about 5%, 10%, 25%, 50%, 75%, 100%, 150%, 200%, 300%, 400%, 500% or more compared to the pH and/or release in the absence of a composition of the present invention. As used herein, the terms "reduce," "reduces," "reduced," "reduction" and similar terms refer to a decrease in the pH and/or release of at least about 5%, 10%, 25%, 35%, 50%, 75%, 80%, 85%, 90%, 95%, 97% or more compared to the pH and/or release in the absence of a composition of the present invention.

"Contact," as used herein in reference to a composition of the present invention (i.e., a first composition) and a second composition, refers to direct and/or indirect exposure of at least one component in the first composition to the second composition. Contact of the first composition and second composition may be accomplished by any means, such as, but not limited to, by mixing, combining, applying to same area or region, and the like, and in some embodiments may optionally form a combined composition of the present invention. For example, a first composition may come into direct contact with a second composition, such as, but not limited to, by mixing and/or combining the first composition and second composition to form a combined composition prior to, during, and/or after topical application to a subject. Direct contact of a first composition and second composition may occur by applying one or more layers of the second composition onto a subject and then applying one or more layers of the first composition onto a subject or vice versa to optionally form a combined composition. Indirect contact may occur by applying a second composition onto a subject and then applying a first composition onto a subject through a substrate, such as, but not limited to, a cloth, bandage, gauze, and the like, or vice versa to optionally form a combined composition.

According to some embodiments of the present invention, upon contact of a composition of the present invention and a second composition, a composition of the present invention is configured to modulate the release of an API present in the second composition, such as, but not limited to, an NO releasing API. In some embodiments, a water present in a composition of the present invention may contact a second composition to modulate the release of an API present in the second composition, such as, but not limited to, an NO releasing API. Alternatively or in addition, in some embodiments, contact of a composition of the present invention with a second composition may modulate the pH of the second composition, thereby modulating the release of an API present in the second composition, such as, but not limited to, an NO releasing API. In some embodiments, a composition of the present invention is configured to supply water to a second composition and/or configured to modulate the pH of a second composition.

In particular embodiments, a composition of the present invention modulates the pH of the second composition such that when the first and second compositions are contacted and/or applied to the skin of a subject, the pH of the second composition and/or combined composition is less that about 8.5, in further embodiments, less than about 7, and in still further embodiments, between about 6 and about 8.

In some embodiments, the pH of a combined composition of the present invention changes upon application of the combined composition to the skin of a subject. In particular embodiments, the pH of a combined composition of the present invention is decreased by the buffering capacity of the skin upon application of the combined composition to the skin of a subject. In some embodiments, the pH of a combined composition of the present invention after application of the combined composition to the skin of a subject is less than the pH of the second composition applied to the skin without the first composition. In embodiments where the release kinetics of the API in a second composition varies with pH, the buffering capacity of the skin may be utilized to modulate release while improving stability of the combined composition after combination and before application. Thus, for example, the pH of a second composition that includes a nitric oxide-releasing macromolecule may be greater than 10 before mixing, 9 after mixing and 8 after application to the skin. With each decrease in pH, the release of nitric oxide from the macromolecule may be increased. Accordingly, taking advantage of the changing pH and buffering capacity of the skin may allow for increased working time (e.g., mixing and application time) for a combined composition of the present invention.

In some embodiments, the second composition is an anhydrous composition. "Anhydrous," as used herein, means that there is no direct addition of water to the second composition when it is being prepared. However, those skilled in the art will recognize that water may be physically and/or chemically absorbed by the second composition and/or by one or more ingredients in the second composition at any time during the preparation, storage, and/or use of the second composition (i.e., indirect addition of water to the second composition). In some embodiments, the term "anhydrous" means that the second composition has a water content of less than 5% by weight of the second composition or any range and/or individual value therein. A second composition may have a water content of less than 5, 4.5, 4, 3.5, 3, 2.5, 2, 1.5, 1, or 0.5%, or any range therein, by weight of the second composition. Water content may be measured by methods known to those of skill in the art, such as, but not limited to, Karl Fischer titration. In certain embodiments, upon contact with a second composition, a composition of the present invention adds water to the second composition and/or the second composition absorbs water from a composition of the present invention.

Exemplary second compositions that may be used and/or placed in contact with a composition of the present invention include, but are not limited to, those described in International Application Publication No. WO 2013/006608, which is incorporated herein by reference in its entirety. An exemplary second composition that may be used and/or placed in contact with a composition of the present invention may comprise an anhydrous composition comprising at least one viscosity increasing agent present in the second composition in an amount of about 0.5% to about 30% by weight of the composition, at least one organic solvent present in the second composition in an amount of about 50% to about 90 by weight of the composition, and at least one humectant present in the second composition in an amount of about 2% to about 20% by weight of the composition. Accordingly, a combined composition of the present invention may comprise at least one polyhydric alcohol, a first viscosity increasing agent, at least one preservative, at least one buffering agent, water, a second viscosity increasing agent, at least one organic solvent, and at least one humectant. The combined composition of the present invention may be buffered to a pH of about 3 to about 8. In certain embodiments, the combined composition of the present invention comprises at least one API, such as, but not limited to, a nitric oxide-releasing active pharmaceutical ingredient.

"Nitric oxide releasing active pharmaceutical ingredient" and "NO releasing API," as used herein, refer to a compound or other composition that provides nitric oxide to the skin of a subject, but is not gaseous nitric oxide. In some embodiments, the NO releasing API includes a nitric oxide-releasing compound, hereinafter referred to as a "NO-releasing compound." An NO-releasing compound includes at least one NO donor, which is a functional group that may release nitric oxide under certain conditions. In some embodiments, the at least one NO donor of an NO-releasing compound releases NO when in contact with a composition of the present invention. In certain embodiments, a composition of the present invention modulates the amount of NO released from an NO-releasing compound and/or the rate of NO released from an NO-releasing compound. In some embodiments, a composition of the present invention increases the amount of NO released from an NO-releasing compound and/or the rate of NO released from an NO-releasing compound.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 μm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Application Publication No. 2009/0214618, the disclosure of which is incorporated by reference herein in its entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

In some embodiments, a composition of the present invention may increase the amount of NO released from a composition compared to the amount of NO released from the composition in the absence of a composition of the present invention over the same period of time. In certain embodiments, a composition of the present invention may increase the amount of NO released by at least about 10%, 20%, 30%, 40%, 50%, 60%, 70%, 80%, 90, or more, or any range and/or individual value therein compared to the amount of NO released in the absence of a composition of the present invention over the same period of time. A composition of the present invention may release between about 1.5 and about 100 times more NO than the amount of NO released in the absence of a composition of the present invention over the same period of time or any range and/or individual value therein, such as, but not limited to between about 2 and 10 times more NO or between about 5 and about 50 times more NO.

Figure 7:
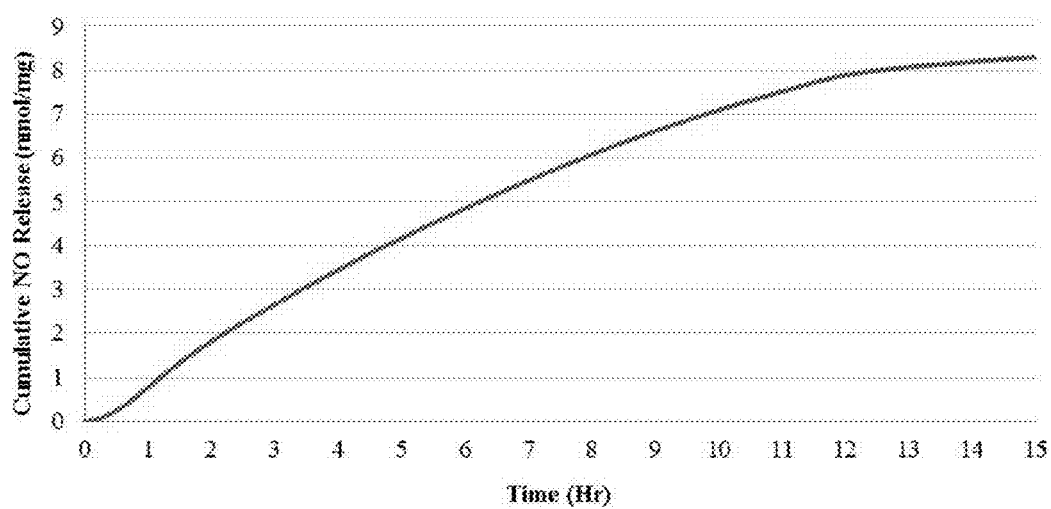
FIG. 7 shows the in vitro nitric oxide release profile for a 2% Nitricil™ NVN1 Gel formulation over time.
Figure 8:
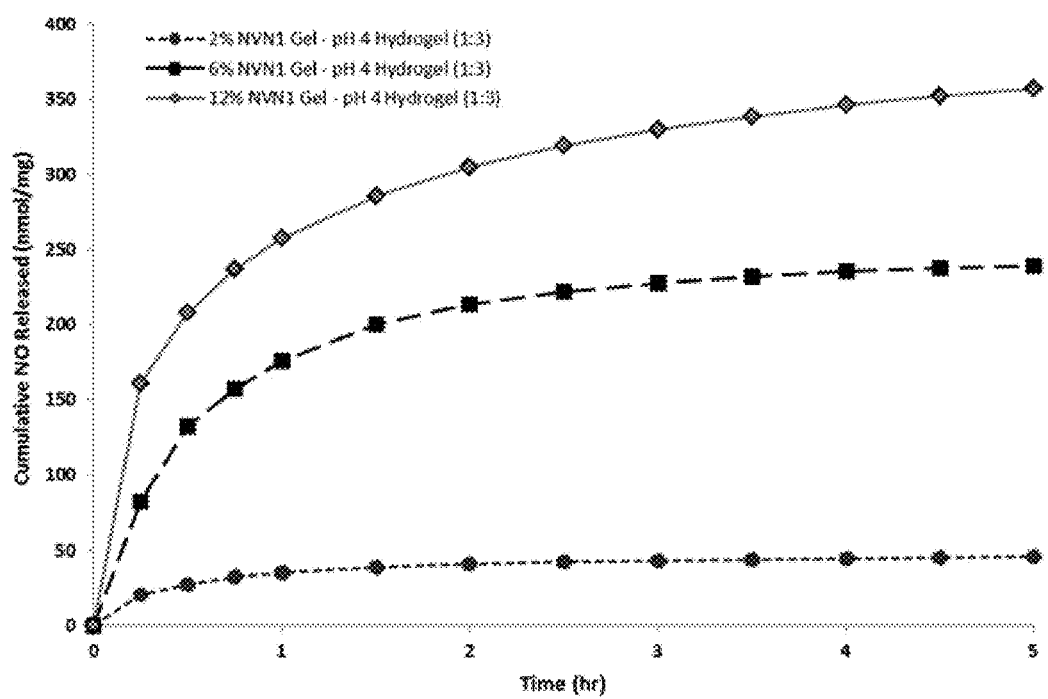
FIG. 8 shows the in vitro nitric oxide release profiles for 2%, 6%, and 12% Nitricil™ NVN1 Gel formulations upon mixing with the hydrogel at pH 4 over time.

For example, the effect a composition of the present invention may have on the amount of NO released can be seen in FIGS. 7 and 8. FIG. 7 shows the in vitro nitric oxide release profile for a 2% Nitricil™ NVN1 Gel having a formulation as set forth in Table 9 over time. FIG. 8 shows the in vitro nitric oxide release profiles for the 2% Nitricil™ NVN1 Gel and a 6% and 12% Nitricil™ NVN1 Gel having formulations as set forth in Table 9 upon mixing with a hydrogel composition of the present invention at pH 4 having a formulation as set forth in Table 10 in a 1:3 ratio (gel:hydrogel) over time. As can be seen from FIGS. 7 and 8 the cumulative NO release for the 2% Nitricil™ NVN1 Gel increased when in contact with a composition of the present invention.

TABLE 9

Composition of the 2%, 6%, and 12% Nitricil ™ NVN1 gels.

| Component | Gel Vehicle | 2% | 6% | 12% |
|---|---|---|---|---|
| Isopropyl alcohol | 85.5 | 83.5 | 80.5 | 74.5 |
| Hexylene glycol | 10.0 | 10.0 | 10.0 | 10.0 |
| Cyclomethicone | 2.5 | 2.5 | 2.5 | 2.5 |
| Hydroxypropyl cellulose | 2.0 | 2.0 | 1.0 | 1.0 |
| Nitricil ™ NVN1 | 0 | 2.0 | 6.0 | 12.0 |

TABLE 10

Composition of the hydrogel with a pH of 4.

| Component | % w/w |
|---|---|
| Purified water | 89.1 |
| Glycerin | 10.0 |
| Carbopol ® 974P | 0.5 |
| Sorbic acid | 0.2 |
| Trolamine | 0.2 |

According to embodiments of the present invention, a kit may be provided. In some embodiments, a kit of the present invention may comprise a first composition comprising a composition of the present invention as described herein and a second composition. The first composition may comprise at least one polyhydric alcohol present in an amount of about 1% to about 30% by weight of the composition, at least one viscosity increasing agent present in an amount of about 0.1% to about 5% by weight of the composition, and water present in an amount of about 70% to about 99% by weight of the composition. The second composition may comprise an API, such as, but not limited to, an NO releasing API. In some embodiments, the second composition may comprise at least one viscosity increasing agent present in the second composition in an amount of about 0.5% to about 30% by weight of the composition, at least one organic solvent present in the second composition in an amount of about 50% to about 90 by weight of the composition, and at least one humectant present in the second composition in an amount of about 2% to about 20% by weight of the composition. In particular embodiments, the second composition comprises an anhydrous alcohol gel containing a nitric oxide-releasing polysiloxane macromolecule as described in International Application Publication No. WO 2013/006608.

In some embodiments, a kit of the present invention comprises an aqueous composition, an organic composition, and an API that may be stable and/or soluble in the aqueous composition or the organic composition. A kit of the present invention may be configured to mix the two compositions upon dispensing and/or for application to a subject and/or may be configured to provide a combined composition with increased performance and/or activity of the API compared to the performance and/or activity of the API in the absence of one of the compositions and/or the combined composition.

A kit of the present invention may separately store a first composition of the present invention and a second composition. In some embodiments, a kit of the present invention may contact the first composition and second composition, such as, but not limited to, by mixing the compositions, prior to application to a subject.

In use, a first composition and a second composition may be mixed together and then applied to the skin of a subject. In other embodiments, a second composition is applied to the skin of a subject and then a first composition is applied over the second composition. In some embodiments, the ratio of a first composition to a second composition that is applied to a subject is about 5:1 or less, in further embodiments, about 4:1 or less, about 3:1 or less, about 2:1 or less or about 1:1. In particular embodiments, the ratio is about 3:1. In further embodiments, the ratio is about 1:1.

Providing a first composition and a second composition that are combined upon application to the skin of a subject may allow for a longer shelf life of a kit of the present invention than if the compositions were stored together mixed together in the kit. For example, the formulation and loading of API in the second composition may provide a stable product with a long shelf life. Thus, for example, pH and water content of the second composition may be adjusted to reduce or minimize release of a water activated API so as to provide a composition that is stable at room temperature. The first composition may then be combined with the second composition to adjust the combined pH and provide water to activate the API. The second composition may be combined with the first composition in differing ratios to provide a desired release, pH and/or dose in the combined composition. Such an approach may allow for a single manufacturing process to be utilized for production of a more complex and costly second composition and then particular products defined by the composition and/or quantity of the first composition with which the second composition is mixed.

As will be appreciated by those of skill in the art in light of the present disclosure, the hydrogels described herein may provide means for adjusting the pH of a pharmaceutical composition as well as means for activating an API of a pharmaceutical composition. In particular embodiments, the hydrogels of the present invention provide means for reducing the pH of an anhydrous pharmaceutical composition comprising a diazeniumdiolate modified co-condensed polysiloxane macromolecule. In further embodiments, the hydrogels of the present invention provide means for releasing nitric oxide from an anhydrous pharmaceutical composition comprising a diazeniumdiolate modified co-condensed polysiloxane macromolecule.

According to some embodiments, a method of the present invention comprises administering a composition of the present invention to the skin of a subject. In certain embodiments, the composition is topically administered. The composition may comprise at least one API, such as, but not limited to, a nitric oxide-releasing active pharmaceutical ingredient; a second viscosity increasing agent; at least one organic solvent; at least one humectant; at least one polyhydric alcohol; a first viscosity increasing agent; at least one preservative; and water. A method of the present invention may comprise forming an admixture prior to and/or during administering the composition of the present invention. An admixture may be prepared by mixing or combining a composition comprising at least one API, such as, but not limited to, a nitric oxide-releasing active pharmaceutical ingredient; a second viscosity increasing agent; at least one organic solvent; and at least one humectant, and a composition comprising at least one polyhydric alcohol; a first viscosity increasing agent; at least one preservative; and water.

In some embodiments, a method of the present invention comprises delivering a therapeutically effective amount of nitric oxide to the skin of a subject. As used herein, the term "therapeutically effective amount" refers to an amount of a nitric oxide that elicits a therapeutically useful response in a subject. Those skilled in the art will appreciate that the therapeutic effects need not be complete or curative, as long as some benefit is provided to the subject.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable, Human subjects of both genders and at any stage of development (i.e., neonate, infant, juvenile, adolescent, adult) may be treated according to the present invention. In some embodiments of the present invention, the subject is a mammal and in certain embodiments the subject is a human, Human subjects include both males and females of all ages including fetal, neonatal, infant, juvenile, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and canaries), and birds in ovo.

The methods of the present invention may also be carried out on animal subjects, particularly mammalian subjects such as mice, rats, dogs, cats, livestock and horses for veterinary purposes, and/or for drug screening and drug development purposes.

The present invention is explained in greater detail in the following non-limiting Examples.

EXAMPLES

Example 1

Unbuffered hydrogel formulations with pH values ranging between 3 and 7 were developed. Several pH 6 hydrogel formulations were manufactured with varying levels of carbomer Carbopol® 974P to investigate the effects on viscosity and gel rheology. The effect of preservatives such as sorbic acid, benzoic and parabens were also investigated on the unbuffered hydrogel rheology and viscosity. The manufactured hydrogel formulations were used in measuring the admixture pH values (Example 2) with Nitricil™ NVN1 topical gel formulations comprising isopropyl alcohol (IPA) and varying strengths of Nitricil™ NVN1, and in establishing in vitro nitric oxide (NO) release kinetics (Example 3). A buffered pH 4 hydrogel with 0.1% w/w citric acid using Carpobol® 980P and a buffered pH 6 hydrogel using Carbopol® ETD 2020NF polymer with 0.2% w/w 0.1M phosphate buffer were also formulated.

For all formulations provided in Tables 1 and 2, United States Pharmacopeia (USP) grade water and anhydrous glycerol were mixed in either a 0.5-L or 2-L glass beaker using an IKA overhead mixer at ambient temperature. For the hydrogel formulations containing a preservative such as sorbic acid, benzoic acid, and methyl- and propyl-paraben, the preservative was added to the water and glycerol solution and heated using a hot plate to 70° C. for complete dissolution to occur. Once dissolution occurred, the solution was cooled down to ambient temperature. The next step in each experiment was to slowly transfer a Carbopol® polymer to the beaker with constant agitation using a combination of overhead stirring and homogenization using the IKA T-18 mixer at speeds of 3-4 for 20-30 seconds. A clear solution formed after 20 minutes indicating complete polymer dissolution. While under continuous agitation, the pH of the un-neutralized mixture was measured initially and trolamine was used as a neutralizing agent in a quantity sufficient (QS) to adjust the pH to the desired value and thicken the hydrogel. Finally, once the desired pH was obtained, a final quantity of water was added to reach the desired target batch size. For Batch Lot 112331, titanium dioxide was introduced into the hydrogel as a masking agent.

TABLE 1

Unbuffered hydrogel formulations without a preservative

| | Hydrogel Formulation [% w/w composition] | | | | | |
|---|---|---|---|---|---|---|
| Ingredient | Batch lot: 112333 | Batch lot: 112335 | Batch lot: 112337 | Batch lot: 112339 | Batch lot: 112345 | Batch lot: 112353 |
| Anhydrous Glycerol, ACS | 10.0 | 10.0 | 10.0 | 10.0 | 10.0 | 10.0 |

TABLE 1-continued

Unbuffered hydrogel formulations without a preservative

| | Hydrogel Formulation [% w/w composition] | | | | | |
|---|---|---|---|---|---|---|
| Ingredient | Batch lot: 112333 | Batch lot: 112335 | Batch lot: 112337 | Batch lot: 112339 | Batch lot: 112345 | Batch lot: 112353 |
| Carbomer Homopolymer Type A, NF, Carbopol ® 974P | 1.0 | 0.5 | 0.2 | 0.3 | 0.4 | 0.5 |
| Purified Water, USP | 86.5 | 86.5 | 86.5 | 86.5 | 85.0 | 85.0 |
| Trolamine, NF | QS to pH 7 | QS to pH 6 | QS to pH 6 | QS to pH 6 | QS to pH 4 | QS to pH 4 |
| Purified Water, USP (adjustment) | QS | QS | QS | QS | QS | QS |

TABLE 2

Unbuffered hydrogel formulations with a preservative.

| | Hydrogel Formulation [% w/w composition] | | | | | | |
|---|---|---|---|---|---|---|---|
| Ingredient | Batch lot: 112331 | Batch lot: 112355 | Batch lot: 112357 | Batch lot: 112359 | Batch lot: 112361 | Batch lot: 112363 | Batch lot: 112365 |
| Anhydrous Glycerol, ACS | 10.0 | 10.0 | 10.0 | 10.0 | 10.0 | 10.0 | 10.0 |
| Benzoic Acid, NF | 0.1 | — | — | — | — | — | — |
| Sorbic Acid, NF | 0.1 | — | 0.2 | 0.1 | 0.2 | 0.1 | — |
| Methyl paraben | — | 0.2 | — | — | — | — | 0.2 |
| Propyl paraben | — | 0.05 | — | — | — | — | 0.1 |
| Carbomer Homopolymer Type A, NF, Carbopol 974P | 1.5 | 0.5 | 0.5 | 0.75 | 0.35 | 0.7 | 0.5 |
| Purified Water, USP | 85.0 | 85.0 | 86.5 | 86.5 | 86.5 | 86.5 | 85.0 |
| Titanium dioxide, NF | 0.05 | — | — | — | — | — | — |
| Trolamine, NF | QS to pH 3 | QS to pH 4 | QS to pH 4 | QS to pH 4 | QS to pH 4 | QS to pH 5 | QS to pH 5 |
| Purified Water, USP (adjustment) | QS | QS | QS | QS | QS | QS | QS |

The pH of un-neutralized mixtures with and without preservatives containing anionic Carbopol® polymer 974P was approximately 2.75-3 depending on the polymer concentration. The viscosity of the pH 3 hydrogel was found to be very low as only a small quantity of trolamine was added to adjust the pH to 3 units and therefore the thickening effects were not realized. To fully neutralize the Carbopol® 974P polymer a pH adjustment to 6 or 7 was necessary using trolamine. However, the viscosity of the resultant unbuffered hydrogels was very high at pH 6 and 7. While not wishing to be bound to any particular theory, for dispensing purposes, the concentration of Carbopol® 974P polymer may need to be reduced from 1% w/w to 0.3-0.5% w/w to lower the viscosity at pH 6 and 7. Using Carbopol® 974P polymer concentrations less than 0.3% w/w, while not wishing to be bound to any particular theory, may result in a hydrogel that is not viscous enough and may run off the surface of the skin when applied.

A pH 4 unbuffered hydrogel can be formulated with 0.5% w/w Carbopol® and have adequate viscosity and rheological properties to flow and dispense from a pump but also not run off the surface of the skin when applied. Table 3 shows the viscosity measurements of several unbuffered pH 4 and pH 5 hydrogels containing preservative(s) as described in Table 2.

TABLE 3

Viscosity measurements for unbuffered hydrogels with a preservative.

| Batch Lot | Viscosity [cP] |
|---|---|
| 112355 | 12675 |
| 112357 | 6961 |
| 112359 | 8631 |
| 112361 | 9372 |
| 112363 | 18376 |
| 112365 | 20746 |

The pH 4 hydrogels with a preservative had a viscosity ranging from 7000-12500 cP. The addition of preservative influenced the pH and therefore the neutralization (thickening) process using trolamine. Without wishing to be bound to any particular theory, to account for the presence of preservative and various concentrations of preservative, the level of Carbopol® polymer may need to be adjusted accordingly to obtain consistent viscosity post neutralization with base. Increasing the pH to 5 for an unbuffered hydrogel with preservative resulted in a significant increase in viscosity to approximately 20000 cP.

With Carbopol® 974P polymer, several buffering acids such as citric acid, tartaric acid and lactic acid were used to buffer at a pH of 4, but the hydrogels would instantaneously break down into water. Carbopol® ETD 2020, NF polymer was found to not be suitable for use with buffering agents at concentrations of 1-3% w/w.

A phosphate buffered pH 6 hydrogel was manufactured using 0.2% w/w Carbopol® ETD 2020 NF polymer in USP water and anhydrous glycerol. A 0.1 M stock of potassium phosphate buffer was added at 0.2% w/w to buffer the hydrogel at a pH of 6 units. This hydrogel was used with Nitricil™ NVN1 topical gels containing IPA and various strengths of Nitricil™ NVN1 to determine admixture pH in vitro (Example 2). The pH 6 phosphate buffered hydrogel had the effect of reducing the pH by 0.5 units at several different Nitricil™ NVN1 concentrations ranging from 0.2% to 8% w/w.

A citric acid buffered pH 4 hydrogel containing 0.1% w/w benzoic acid and 0.1% sorbic acid with 1% w/w Carbopol® polymer 980P was successfully compounded at a 0.5-kg scale. The composition of the buffered citric acid hydrogel is listed in Table 4. This buffered hydrogel (Batch lot: 126335) was measured to have a viscosity of 7285 cP. The citric acid buffered hydrogel manufactured was used to determine in vitro and skin surface pH (Example 2) including establishing in vitro nitric oxide release profiles (Example 3).

TABLE 4

Ingredient list and composition of the citric acid buffered pH 4 hydrogel.

| Hydrogel ingredient (Batch lot: 126335) | % w/w composition |
| --- | --- |
| Anhydrous Glycerol, ACS | 10.0 |
| Benzoic Acid, NF | 0.1 |
| Sorbic Acid, NF | 0.1 |
| Citric acid | 0.1 |
| Carbomer Homopolymer Type C, NF, Carbopol 980P | 1 |
| Purified Water, USP | 70 |
| Trolamine, NF | QS to pH 4 |
| Purified Water, USP (adjustment A) | 10 |
| Purified Water, USP (adjustment B) | QS |

Hydrogel formulations covering a range of pH values were formulated. The initial hydrogels formulated were unbuffered and compounded with and without preservatives. Preservatives such as benzoic acid, sorbic acid and parabens were used. Parabens were found to react with Nitricil™ NVN1 IPA topical gels. The pH of the hydrogels was adjusted by varying the quantity of trolamine (neutralizing agent) added. To increase the pH and viscosity, the amount of neutralizing agent added was increased. At pH 6 and 7, the viscosity of the unbuffered hydrogels without preservatives formed was high. In order to reduce the hydrogel viscosity, the Carbopol® polymer concentration was reduced. The addition of preservatives also influenced the initial pH. The amount of polymer and neutralizing agent was adjusted accordingly to reach the desired pH and obtain a viscosity that is not too low as to cause issues with runoff from the surface of the skin and not too high such as to cause issues with product flow and pumping from a dual chamber dispensing device. Attempts were made to manufacture a buffered pH 4 hydrogel using Carpobol® 974P and ETD 2020 polymer with citric acid, lactic acid, and tartaric acid as buffering agents but this resulted in the polymers breaking down into water due to rapid changes in pH.

By switching to Carbopol® 980P, which is a Homopolymer Type C and a longer chain polymer, a 0.1% w/w citric acid buffered pH 4 hydrogel with sorbic acid and benzoic acid was successfully formulated. A pH 6 hydrogel that was buffered with 0.1 M phosphate buffer at 0.2% w/w was also successfully formulated with Carbopol® ETD 2020 polymer.

Example 2

A series of experiments were carried out to determine the final admixture pH of Nitricil™ NVN1 topical gels containing IPA and having different strengths of Nitricil™ NVN1 ranging from 0.2-12% w/w with unbuffered and buffered hydrogel formulations having a pH ranging from 4 to 6 at different hydrogel to Nitricil™ NVN1 topical gel ratios ranging from 1:1 to 3:1 (Hydrogel to Nitricil™ NVN1 topical gel). The effect of hydrogel pH, mixing ratio of hydrogel to Nitricil™ NVN1 IPA topical gel, and Nitricil™ NVN1 strength on the final admixture pH was investigated. The aim of the experiments was to determine whether a final admixture pH ranging between 6 to 8 could be obtained.

For all in vitro pH admixture measurements, approximately 1-g quantity of Nitricil™ NVN1 Topical IPA Gel was dispensed into a tared weigh boat using either a 1 mL plastic syringe or directly dispensed from aluminum tubes. Once approximately 1 g quantity was dispensed, the weigh boat was re-tared. A pre-determined quantity of hydrogel ranging from 1 to 3-g was then dispensed into the weigh boat using a 1 mL syringe. The admixture was then mixed using pH probe (Beckman φ350 pH meter) until a single steady state pH measurement was recorded. All dispensing was done on a weight basis.

A pH 6 phosphate buffered hydrogel, an unbuffered pH 4 hydrogel, and an unbuffered pH 6 hydrogel were used to determine admixture pH values as shown in Table 5.

TABLE 5

Hydrogel formulations used in the initial admixture pH determinations.

| | % w/w | | |
| --- | --- | --- | --- |
| Ingredient | pH 4 | pH 6 | pH 6 (Buffered) |
| Purified Water, USP | 85.0 | 85.0 | 85.0 |
| Glycerol, NF | 10.0 | 10.0 | 10.0 |
| Carbomer Homopolymer Type A, NF Carbopol 974P | 1.0 | 0.3 | — |
| Carbomer Interpolymer Type B, NF Carbopol ETD2020NF | — | — | 0.5 |
| Trolamine, NF | QS to pH 4 | QS to pH 6 | QS to pH 6 |
| Purified Water, USP | QS | QS | — |
| 0.1M Phosphate Buffer (pH 6.0) | — | — | QS |

FIG. 1 shows the effect of Nitricil™ NVN1 Topical Gel strength, hydrogel pH, and hydrogel to Nitricil™ NVN1 IPA Topical Gel ratio on the admixture pH. The admixture pH results demonstrate that in order to achieve a pH of 8 for the final admixture, Nitricil™ NVN1 Topical Gel at or below 6% w/w Nitricil™ NVN1 could be used in combination with the hydrogel pH 4 at either a 1:1 or 3:1 ratio. At strengths of 8% w/w Nitricil™ NVN1 or greater, the strong buffering properties of Nitricil™ NVN1 start to heavily influence the pH of the admixture over the range of hydrogel pH's and ratios evaluated. Significant foaming (indicating nitric oxide release) was observed at strengths greater than 4% w/w Nitricil™ NVN1 when mixing with both pH 4 and pH 6 hydrogels. This was observed even at high pH admixture values greater than 8 when using pH 6 hydrogels. The 1:3 ratio of Nitricil™ NVN1 Topical Gel and hydrogel buffered at pH 6 allowed the resulting pH of the admixture to be maintained below pH 8 for Nitricil™ NVN1 Topical Gel strengths up to 2% w/w Nitricil™ NVN1. Buffering the hydrogel with phosphate at pH 6 helped reduce the final admixture pH at both 1:1 and 1:3 mixing ratios of hydrogel to Nitricil™ NVN1 IPA Topical Gel.

Further experiments investigated the effect of adding preservatives (e.g., parabens, sorbic acid and benzoic acid) at concentrations ranging between 0.1% to 0.2% w/w to hydrogel formulations adjusted to pH 4 and pH 5. The admixture pH was measured for Nitricil™ NVN1 Topical Gel strengths at 2% w/w and 8% w/w.

Table 6 shows the admixture pH values using both 2% and 8% w/w Nitricil™ NVN1. The results in Table 6 show that the 2% w/w Nitricil™ NVN1 IPA Topical Gel with the pH 4 hydrogel, with and without preservatives, at a ratio of 1:1 provided a resultant admixture pH between 6 and 7.

TABLE 6

Admixture pH values for different pH hydrogels with and without preservative.

| Nitricil™ NVN1 [% w/w] | Hydrogel pH | Preservative | Concentration [% w/w] | Admixture pH |
|---|---|---|---|---|
| 2 | 4 | Methyl- and Propyl-paraben | 0.25 | 6.61 (Gel mixture turns brown) |
| 2 | 4 | Sorbic acid | 0.2 | 5.89 |
| 2 | 4 | Sorbic acid | 0.1 | 6.73 |
| 2 | 4 | No preservative | — | 6.78 |
| 8 | 4 | 0.2% methyl- and 0.5% propyl-paraben | 0.25 | 9.93 |
| 8 | 4 | Sorbic acid | 0.2 | 10.19 |
| 8 | 4 | Sorbic acid | 0.1 | 10.27 |
| 8 | 4 | None | — | 8.25 |
| 8 | 4 | None | — | 10.80 |
| 2 | 5 | Methyl- and Propyl-paraben | 0.25 | 7.15 (Gel mixture turns brown) |
| 2 | 5 | Sorbic acid | 0.2 | 6.81 |
| 2 | 5 | Sorbic acid | 0.1 | 6.94 |

Using methyl- and propyl-paraben as preservatives resulted in the admixture turning brown. Without wishing to be bound to any particular theory, this could be indicative of the formation of degradation product(s). Using pH 5 hydrogels with different preservatives, the admixture pH only increased marginally to about 7.

The surface skin pH of the admixture was also measured for 8% w/w Nitricil™ NVN1 Topical IPA Gel with both a buffered and unbuffered pH 4 hydrogel. The buffered pH 4 hydrogel contained Carbopol® 980P NF polymer with 0.1% w/w citric acid. Benzoic acid and sorbic acid at 0.1% w/w were also used as preservatives in the citric acid buffered pH4 formulated hydrogel.

Figure 2:
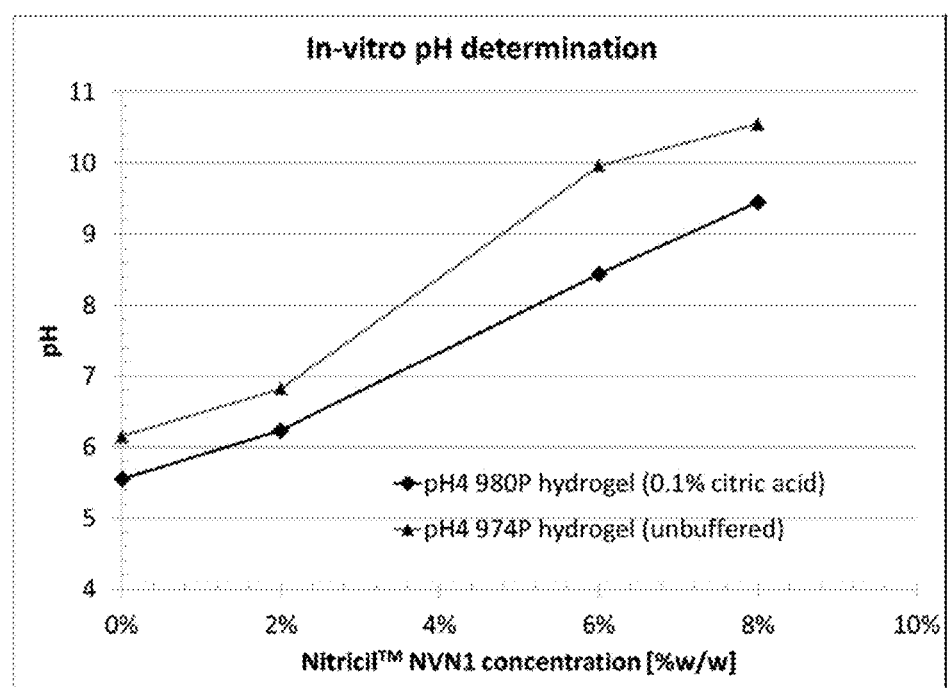
FIG. 2 shows a graph of the in vitro pH determination for Nitricil™ NVN1 topical gels when admixed with an unbuffered or buffered (0.1% citric acid) hydrogel (pH 4).

Further in vitro pH admixture measurements were taken with an unbuffered pH 4 hydrogel (Carbopol® 974P) and buffered pH 4 hydrogel with 0.1% w/w citric acid (Carbopol® 980P) at a 1:1 ratio to confirm observations made from experimental results in Table 6. FIG. 2 shows that at 6% w/w and 8% w/w Nitricil™ NVN1 concentrations when used with an unbuffered pH 4 hydrogel, the admixture pH is around 10 and is comparable with previous results. The use of 0.1% w/w citric acid buffered pH 4 hydrogel has the effect of reducing the admixture pH over a range of Nitricil™ NVN1 concentrations.

Figure 3:
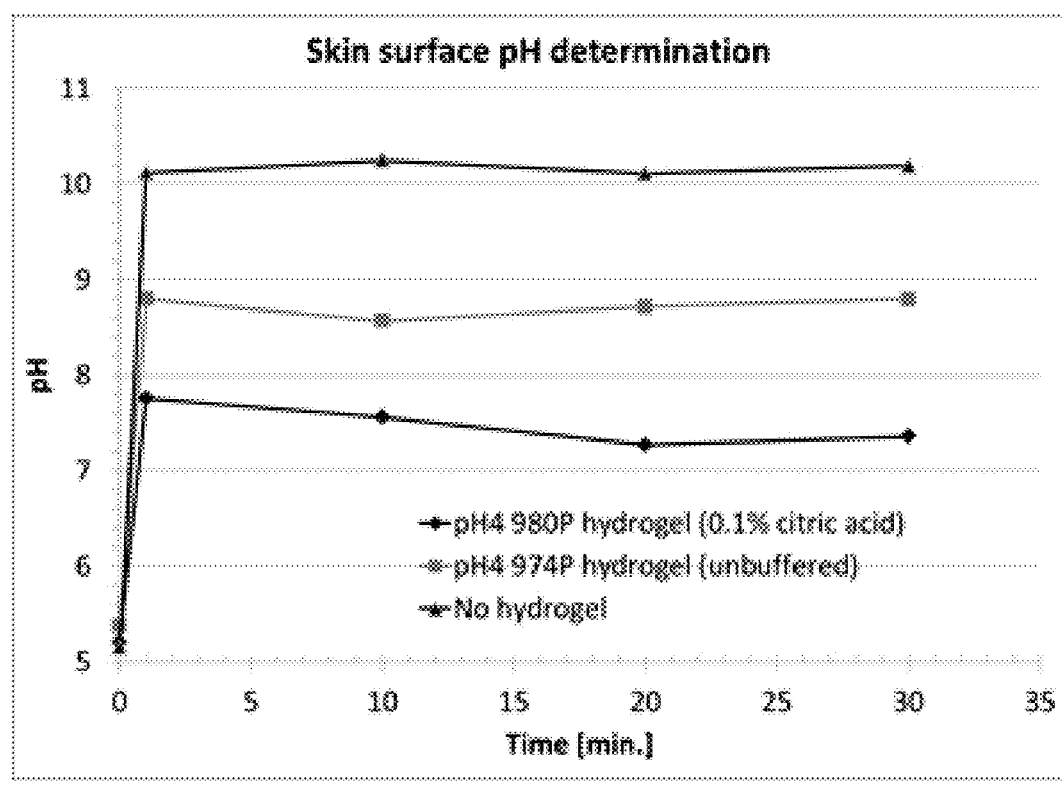
FIG. 3 shows a graph of the skin surface pH determination for admixtures of an unbuffered or buffered pH 4 hydrogel and an 8% w/w Nitricil™ NVN1 Topical Gel.

An in vitro skin surface pH determination investigation was also performed. FIG. 3 shows that the skin, which has a pH range of between 5 and 6, provides some degree of buffering capability. Application of an unbuffered pH 4 hydrogel mixed with the 8% w/w Nitricil™ NVN1 IPA Topical Gel resulted in a skin pH just below 9. The pH remained consistent over 30 minutes. However, when the pH 4 hydrogel buffered with 0.1% w/w citric acid was used (including 0.1% w/w benzoic acid and 0.1% w/w sorbic acid as preservatives) with the 8% w/w Nitricil™ NVN1 IPA Topical Gel, the skin surface pH was around 7.5.

Without wishing to be bound to any particular theory, the experiments demonstrate that with pH 4 buffered and unbuffered hydrogels at a 1:1 and 3:1 ratio, the final admixture pH can be maintained between 5 to 8 for Nitricil™ NVN1 concentrations ranging between 0.2% w/w and 4% w/w. With a pH 4 unbuffered hydrogel at a 3:1 ratio it is possible to maintain the admixture pH below 8 units for Nitricil™ NVN1 concentrations up to 8% w/w. With a buffered pH 6 hydrogel it is possible to maintain the pH below 8 at Nitricil™ NVN1 concentrations of 2% w/w or less. To maintain the admixture pH value below 8, a concentration of 1% w/w Nitricil™ NVN1 or less may be used with an unbuffered pH 6 hydrogel. The use of preservatives in hydrogels has no to little effect on the admixture pH. The use of pH 4 hydrogels that are unbuffered and buffered at a ratio of 1:1 resulted in pH values greater than 8 units. However, when applied to the skin the pH measurement at the surface decreases as the skin offers some buffering capacity. To obtain a skin surface admixture pH less than 8 units, a pH 4 hydrogel that is buffered with 0.1% w/w citric acid and containing 0.1% w/w benzoic acid and sorbic acid can be used. However, an unbuffered pH 4 hydrogel gave a skin surface pH value of greater than 8.5 when compared to pH of 10 units from in vitro testing results.

Example 3

In vitro release testing was performed using both a single channel and multi-channel Nitric Oxide Analyzer. An analytical balance was used to weight Nitricil™ NVN1 Topical Gel and hydrogel samples. Approximately 50-mg of the Nitricil™ NVN1 Topical Gel sample and either ~50 mg or ~150 mg hydrogel sample were transferred to a single, pre-cut weigh boat without allowing contact between the samples. The two samples were mixed for approximately 5 sec., and then immediately placed into a clean, dry 50-mL NO measurement cell maintained at 37° C. The real-time in vitro release of nitric oxide from the combined Nitricil™ NVN1 Topical Gel/Hydrogel samples was determined using the following instrumental parameters:

1. Moist Nitrogen Flow Rate: 112-115 ml/min
2. Sample Temperature: 37° C.
3. Detection: Nitric Oxide by Chemiluminescence
4. Data Acquisition Frequency: 1 Hz, Irregular Sequential Alternating
5. Duration: Time at which NO release rate decreases linearly (NLT 8 hr)
6. Acquisition Software: NovanWare v 1.05

Conversion from parts per billion (PPB) NO to moles nitric oxide was achieved by measuring the nitric oxide generated from a known amount of sodium nitrite in a solution of potassium iodide to acquire a PPB-to-mole conversion factor. Any gaps in real-time nitric oxide release data resulting from multichannel operation were filled in by using a linear interpolation program. For any sample that was not measured to exhaustion of nitric oxide, a linear extrapolation to zero release of the last ~5000 sec of release was performed. Real-time nitric oxide release data was then integrated, resulting in a total nitric oxide accumulation curve. Nitric oxide release parameters such as $C_{max}$ (i.e., the maximum concentration of NO released), $T_{max}$ (i.e., the time at which $C_{max}$ is achieved), Cumulative Nitric Oxide Released (i.e., the sum of all data points per unit time), and Time to Half of Total Released ($T_{50}$) (i.e., the time at which 50% of the cumulative NO is released) were calculated from both the real time and total accumulation nitric oxide release curves. All of the above calculations were performed automatically in custom-built data processing software (NovanWare v 1.05).

The results from in vitro release testing, along with the respective pH of the admixtures are summarized in Table 7 below.

pronounced for mixtures containing a 1:3 ratio with a pH 4 hydrogel versus 1:1 and 1:3 ratios with a pH 6 hydrogel. Further in vitro studies were performed using a pH 4 buffered citric acid hydrogel with preservative. Measurements were repeated in triplicate. The admixture was mixed for a period of 15 seconds prior to loading into the measurement cell. The results for the in vitro nitric oxide release tests are shown in Table 8.

TABLE 8

Results summary for pH and in vitro release testing of Nitricil ™ NVN1 topical gel using citric acid pH 4 buffered hydrogel.

| Sample | $C_{max}$ (nmol/ mg · s) | Cumulative NO (nmol/mg) | $T_{max}$ (min) | $T_{50}$ (min) | pH of Mixture |
|---|---|---|---|---|---|
| 2% Gel/Hydrogel pH 4 (citric acid buffer) #1 | 0.162 | 71 | 1 | 8 | 6.2 |

TABLE 7

Results summary for pH and in vitro release testing of Nitricil ™ NVN1 topical gel.

| Sample | Ratio | $C_{max}$ (nmol/mg/s) | Cumulative NO (nmol/mg) | $T_{max}$ (min) | $T_{50}$ (min) | pH |
|---|---|---|---|---|---|---|
| 0.2% Gel/Hydrogel pH 4 | 1:1 | 0.009 | 5 | 1 | 14 | 5.5 |
| 0.2% Gel/Hydrogel pH 4 | 1:3 | 0.008 | 4 | 1 | 13 | 5.0 |
| 0.2% Gel/Hydrogel pH 6 | 1:1 | 0.003 | 4 | 1 | 52 | 6.6 |
| 0.2% Gel/Hydrogel pH 6 | 1:3 | 0.007 | 6 | 1 | 37 | 6.7 |
| 0.5% Gel/Hydrogel pH 4 | 1:1 | 0.016 | 17 | 2 | 23 | 5.6 |
| 0.5% Gel/Hydrogel pH 4 | 1:3 | 0.037 | 17 | 1 | 7 | 5.1 |
| 0.5% Gel/Hydrogel pH 6 | 1:1 | 0.011 | 12 | 2 | 30 | 7.3 |
| 0.5% Gel/Hydrogel pH 6 | 1:3 | 0.014 | 15 | 1 | 41 | 7.0 |
| 1% Gel/Hydrogel pH 4 | 1:1 | 0.042 | 37 | 2 | 17 | 5.8 |
| 1% Gel/Hydrogel pH 4 | 1:3 | 0.075 | 39 | 1 | 8 | 5.3 |
| 1% Gel/Hydrogel pH 6 | 1:1 | 0.018 | 30 | 3 | 43 | 8.3 |
| 1% Gel/Hydrogel pH 6 | 1:3 | 0.038 | 41 | 2 | 51 | 7.2 |
| 2% Gel/Hydrogel pH 4 | 1:1 | 0.092 | 73 | 1 | 24 | 6.8 |
| 2% Gel/Hydrogel pH 4 | 1:3 | 0.062 | 50 | 1 | 24 | 5.5 |
| 2% Gel/Hydrogel pH 6 | 1:1 | 0.045 | 29 | 1 | 50 | 8.6 |
| 2% Gel/Hydrogel pH 6 | 1:3 | 0.070 | 71 | 2 | 58 | 8.8 |
| 4% Gel/Hydrogel pH 4 | 1:1 | 0.118 | 126 | 1 | 36 | 8.2 |
| 4% Gel/Hydrogel pH 4 | 1:3 | 0.175 | 138 | 2 | 18 | 7.1 |
| 4% Gel/Hydrogel pH 6 | 1:1 | 0.018 | 88 | 3 | 230 | 10.8 |
| 4% Gel/Hydrogel pH 6 | 1:3 | 0.068 | 107 | 2 | 71 | 9.9 |
| 6% Gel/Hydrogel pH 4 | 1:1 | 0.151 | 138 | 2 | 23 | 7.6 |
| 6% Gel/Hydrogel pH 4 | 1:3 | 0.240 | 220 | 1 | 25 | 6.6 |
| 6%/Hydrogel pH 6 | 1:1 | 0.020 | 109 | 3 | 155 | 11.3 |
| 6%/Hydrogel pH 6 | 1:3 | 0.077 | 129 | 2 | 43 | 10.5 |
| 8% Gel/Hydrogel pH 4 | 1:1 | 0.120 | 180 | 1 | 67 | 8.3 |
| 8% Gel/Hydrogel pH 4 | 1:3 | 0.187 | 239 | 1 | 25 | 6.9 |
| 8%/Hydrogel pH 6 | 1:1 | 0.037 | 134 | 5 | 247 | 10.4 |
| 8%/Hydrogel pH 6 | 1:3 | 0.056 | 109 | 9 | 43 | 10.1 |
| 12% Gel/Hydrogel pH 4 | 1:1 | 0.159 | 242 | 3 | 94 | 9.6 |
| 12% Gel/Hydrogel pH 4 | 1:3 | 0.357 | 364 | 5 | 28 | 8.4 |
| 12% Gel/Hydrogel pH 6 | 1:1 | 0.016 | 184 | 5 | 371 | 11.4 |
| 12% Gel/Hydrogel pH 6 | 1:3 | 0.074 | 282 | 5 | 166 | 11.0 |

Figure 4:
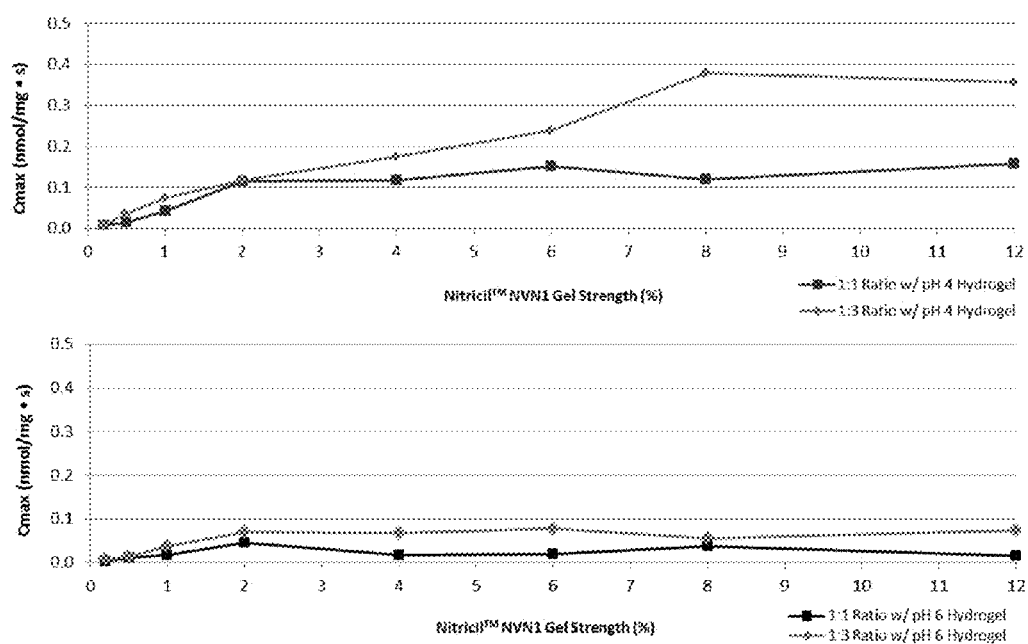
FIG. 4 shows a graph of the effects of Nitricil™ NVN1 Topical Gel strength and hydrogel ratio on $C_{max}$.
Figure 5:
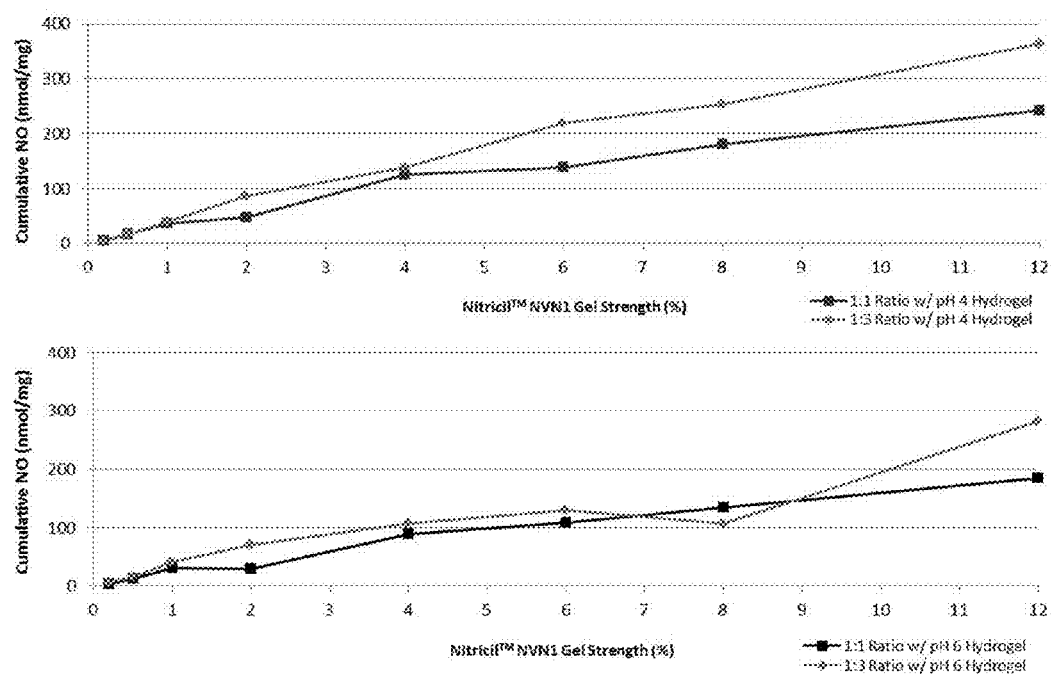
FIG. 5 shows a graph of the effects of Nitricil™ NVN1 Topical Gel strength and hydrogel ratio on cumulative nitric oxide (NO) release.
Figure 6:
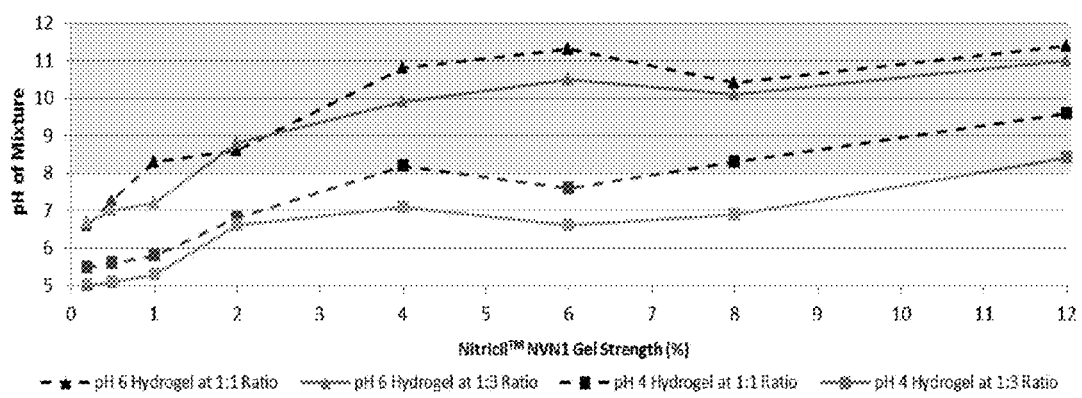
FIG. 6 shows a graph of the effects of unbuffered hydrogel pH and ratio on admixture pH with respect to Nitricil™ NVN1 Topical Gel strength.

FIG. 4 illustrates how $C_{max}$ from each mixture is impacted by the ratio of the mixture, the pH of the hydrogel, and the concentration of NVN1. In general, for pH 4 hydrogels the $C_{max}$ increased with increasing NVN1 concentration. This effect is more pronounced with mixtures containing 1:3 Nitricil™ NVN1 IPA Topical Gel to hydrogel. FIG. 5 shows the increase in cumulative nitric oxide released with increasing Nitricil™ NVN1 concentrations.

At all Nitricil™ NVN1 concentrations, mixtures containing pH 4 hydrogels generally release more of their nitric oxide payload at higher $C_{max}$ (FIG. 4) and with a shorter half-life than with pH 6 hydrogels. This effect is more TABLE 8-continued Results summary for pH and in vitro release testing of Nitricil ™ NVN1 topical gel using citric acid pH 4 buffered hydrogel.

| Sample | $C_{max}$ (nmol/ mg · s) | Cumulative NO (nmol/mg) | $T_{max}$ (min) | $T_{50}$ (min) | pH of Mixture |
|---|---|---|---|---|---|
| 2% Gel/Hydrogel pH 4 (citric acid buffer) #2 | 0.109 | 59 | 1 | 10 | |
| 2% Gel/Hydrogel pH 4 (citric acid buffer) #3 | 0.148 | 60 | 1 | 8 | |

TABLE 8-continued

Results summary for pH and in vitro release testing of Nitricil™ NVN1 topical gel using citric acid pH 4 buffered hydrogel.

| Sample | $C_{max}$ (nmol/ mg · s) | Cumulative NO (nmol/mg) | $T_{max}$ (min) | $T_{50}$ (min) | pH of Mixture |
|---|---|---|---|---|---|
| Average | 0.140 | 63 | 1 | 9 | |
| 8% Gel/Hydrogel pH 4 (citric acid buffer) #1 | 0.200 | 167 | 1 | 30 | 9.5 |
| 8% Gel/Hydrogel pH 4 (citric acid buffer) #2 | 0.218 | 182 | 1 | 26 | |
| 8% Gel/Hydrogel pH 4 (citric acid buffer) #3 | 0.250 | 185 | 1 | 23 | |
| Average | 0.256 | 178 | 1 | 26 | |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A composition comprising:
an aqueous composition in an admixture with an anhydrous composition in a ratio of the aqueous composition to the anhydrous composition of about 3:1 or less;
wherein the aqueous composition is a buffered hydrogel and comprises:
a first viscosity increasing agent in an amount of 0.6% to 5% by weight of the aqueous composition, wherein the first viscosity increasing agent is a cellulose ether or a carboxypolymethylene;
at least one polyhydric alcohol in an amount of 1% to 30% by weight of the aqueous composition;
at least one buffering agent;
water; and
optionally at least one preservative;
wherein the anhydrous composition is an alcohol gel and comprises:
a second viscosity increasing agent in an amount of 0.5% to 30% by weight of the anhydrous composition;
at least one alcohol in an amount of 50% to 90% by weight of the anhydrous composition;
at least one humectant in an amount of 2% to 20% by weight of the anhydrous composition; and
diazeniumdiolate modified polysiloxane macromolecules comprising a co-condensed siloxane network.

2. The composition of claim 1, wherein the aqueous composition is in the admixture with the anhydrous composition in a ratio of about 3:1.

3. The composition of claim 1, further comprising at least one water repellant.

4. The composition of claim 1, further comprising at least one neutralizing agent.

5. The composition of claim 1, wherein the composition has a pH of about 3 to about 8 when topically applied to skin of a subject.

6. The composition of claim 1, wherein the composition is cosmetically elegant.

7. The composition of claim 1, wherein the diazeniumdiolate modified polysiloxane macromolecules release nitric oxide in an amount of at least 50% over a period of time of about 3 hours or less after topical application of the composition to skin of a subject.

8. A kit comprising:
a buffered hydrogel having a pH in a range of 3 to 6.5 and comprising:
at least one polyhydric alcohol present in an amount of 1% to 30% by weight of the hydrogel;
a first viscosity increasing agent present in an amount of 0.6% to 5% by weight of the hydrogel, wherein the first viscosity increasing agent is a cellulose ether or a carboxypolymethylene;
at least one buffering agent; and
water; and
an anhydrous alcohol gel comprising:
diazeniumdiolate modified polysiloxane macromolecules comprising a co-condensed siloxane network;
a second viscosity increasing agent present in the anhydrous alcohol gel in an amount of 0.5% to 30% by weight of the anhydrous alcohol gel;
at least one alcohol present in the anhydrous alcohol gel in an amount of about 50% to about 90% by weight of the anhydrous alcohol gel; and
at least one humectant present in the anhydrous alcohol gel in an amount of about 2% to about 20% by weight of the anhydrous alcohol gel.

9. The kit of claim 8, wherein the buffered hydrogel and the anhydrous alcohol gel are separately stored.

10. A method of increasing the release of nitric oxide from the anhydrous alcohol gel of claim 8 comprising:
contacting the anhydrous alcohol gel with the buffered hydrogel of claim 8 to provide a combined composition; and
applying the combined composition to the skin of a subject.

11. The composition of claim 1, wherein the aqueous composition is in the admixture with the anhydrous composition in a ratio of about 1:1.

12. The composition of claim 1, wherein the first viscosity increasing agent comprises a carboxypolymethylene, the at least one polyhydric alcohol is glycerin, the at least one buffering agent is lactic acid, and water is present in an amount of about 70% to about 99% by weight of the aqueous composition.

13. The composition of claim 1, wherein the first viscosity increasing agent comprises a carboxymethyl cellulose, the at least one polyhydric alcohol is glycerin, and the at least one buffering agent comprises potassium phosphate.

14. The composition of claim 1, wherein the second viscosity increasing agent is hydroxypropyl cellulose, the at least one alcohol is ethyl alcohol or isopropyl alcohol, and the at least one humectant is hexylene glycol.

15. The composition of claim 1, wherein the at least one alcohol is isopropyl alcohol and the composition further comprises cyclomethicone.

16. The composition of claim 14, wherein the first viscosity increasing agent comprises a carboxypolymethylene, the at least one polyhydric alcohol is glycerin, and the at least one buffering agent is lactic acid.

17. The composition of claim 14, wherein the first viscosity increasing agent comprises a carboxymethyl cellulose, the at least one polyhydric alcohol is glycerin, and the at least one buffering agent comprises potassium phosphate.

18. The composition of claim 1, wherein the buffered hydrogel has a pH in a range of about 3 to about 6.5.

19. The composition of claim 1, wherein the composition comprising the aqueous composition and the anhydrous composition is buffered to a pH of about 3 to about 8 for at least 5 minutes.

20. The composition of claim 1, wherein the composition comprising the aqueous composition and the anhydrous composition is buffered to a pH of about 3 to about 8 for at least 60 minutes.

21. The kit of claim 8, wherein the second viscosity increasing agent is hydroxypropyl cellulose, the at least one alcohol is ethyl alcohol or isopropyl alcohol, and the at least one humectant is hexylene glycol.

22. The kit of claim 21, wherein the at least one alcohol is isopropyl alcohol and the anhydrous alcohol gel further comprises cyclomethicone.

23. The kit of claim 8, wherein the first viscosity increasing agent comprises a carboxypolymethylene, the at least one polyhydric alcohol is glycerin, and the at least one buffering agent is lactic acid.

24. The kit of claim 8, wherein the first viscosity increasing agent comprises a carboxymethyl cellulose, the at least one polyhydric alcohol is glycerin, and the at least one buffering agent comprises potassium phosphate.

\* \* \* \* \*

UNITED STATES PATENT AND TRADEMARK OFFICE
CERTIFICATE OF CORRECTION

PATENT NO. : 9,855,211 B2
APPLICATION NO. : 14/191958
DATED : January 2, 2018
INVENTOR(S) : Doxey et al.

Page 1 of 1

It is certified that error appears in the above-identified patent and that said Letters Patent is hereby corrected as shown below:

In the References:
(56) References Cited, U.S. Patent Documents: Please add the following:
-- 6,319,913 B1 11/2001 Mak et al.
6,479,058 B1 11/2002 McCadden --

Other Publications: Please add the following:
-- Office Action issued for U.S. Patent Application No.:
14/771,138 (12 pages) (mailed Dec. 6, 2017) --

Signed and Sealed this
Fifteenth Day of May, 2018

Andrei Iancu
*Director of the United States Patent and Trademark Office*